United States Patent [19]

Gasson et al.

[11] 3,990,999

[45] Nov. 9, 1976

[54] CATALYST COMPOSITIONS

[75] Inventors: Edward James Gasson, Dollar; Thomas Charles Krosnar, Polmont; Stanley Frederic Marrian, Fife, all of Scotland

[73] Assignee: BP Chemicals International Limited, London, England

[22] Filed: June 10, 1975

[21] Appl. No.: 585,481

[30] Foreign Application Priority Data

June 25, 1974 United Kingdom............... 28095/74

[52] U.S. Cl. ............................................. 252/469
[51] Int. Cl.$^2$..................... B01J 23/18; B01J 23/28
[58] Field of Search............................. 252/467, 469

[56] References Cited

UNITED STATES PATENTS

| | | | |
|---|---|---|---|
| 3,551,470 | 12/1970 | Shaw et al. ...................... | 252/467 X |
| 3,595,911 | 7/1971 | Ball................................. | 252/467 X |
| 3,709,829 | 1/1973 | Gasson............................ | 252/467 X |
| 3,899,516 | 8/1975 | Dickason ........................ | 252/467 X |

*Primary Examiner*—W. J. Shine
*Attorney, Agent, or Firm*—Brooks Haidt Haffner & Delahunty

[57] ABSTRACT

Antimony containing catalysts are promoted by addition of small quantities of molybdenum from 0.5 to 1.0 atom%. Preferred compositions to be promoted contain antimony together with tin together with copper and/or iron and/or titanium.

6 Claims, No Drawings

CATALYST COMPOSITIONS

The present invention relates to catalyst compositions and in particular to catalyst compositions containing antimony, for use in catalysing reactions of organic compounds.

Catalyst compositions containing antimony in the form of an oxide or oxide compositions are well-known for use in catalysing reactions of organic compounds. Thus, for example, it is well-known to use such catalysts which also contain other metals combined in the form of oxides or oxide compositions to catalyse the oxidation of olefins such as propylene or isobutene to produce the corresponding unsaturated aliphatic aldehydes such as acrolein or methacrolein or the unsaturated aliphatic carboxylic acids such as acrylic or methacrylic acids or to catalyse the oxidation of the unsaturated aliphatic aldehydes themselves to produce such corresponding acids or to catalyse the conversion of such olefins and/or aldehydes to the corresponding unsaturated aliphatic nitriles such as acrylonitrile or methacrylonitrile by reaction with ammonia and molecular oxygen or to catalyse the oxidative dehydrogenation of mono-olefins to produce diolefins. In particular it is known from British patent specification No. 876,446 (The Distillers Company Limited) to produce acrylonitrile or methacrylonitrile by a process which comprises reacting at an elevated temperature in the vapour phase propylene or isobutene with oxygen and ammonia over an oxidation catalyst comprising (i) a mixture of the oxides of antimony and tin and/or (ii) a compound of antimony, tin and oxygen.

It has now been found that with such antimony based catalysts it is possible to promote their activity by the addition of certain elements in a compounded form. The addition of some at least of these additional elements to antimony based catalysts is already known. However, according to the present invention it is found that only by incorporation of the additional elements in amounts within a narrow defined range is any benefit obtained.

Thus according to the present invention there is provided a catalyst composition suitable for catalysing the reaction of organic compounds which comprises an oxide composition containing antimony and which has been heat-treated at a temperature between 700° and 900° C in a molecular oxygen containing gas and to which has been added, either before or subsequent to the heat treatment, an oxide or compound of molybdenum or tungsten or mixtures thereof, in amount such as to provide from 0.05 to 1.0 atom % as hereinafter defined of molybdenum and/or tungsten, in the catalyst composition.

By the term "atom %" herein is meant the quotient

<u>100 × number of atoms of the additional metal</u>
Total number of metal atoms in the oxide composition.

It is preferred to add an oxide or compound of molybdenum or tungsten to the heat-treated oxide composition in an amount such as to provide from 0.1 to 0.6 atom % of the molybdenum and/or tungsten.

The oxide composition containing antimony may also contain one or more additional metals combined in the form of oxide or oxide compositions. Suitable metals, among many others include tin, titanium, copper, magnesium, zinc, vanadium, uranium, chromium, manganese, iron, cobalt, nickel, indium, arsenic and tellurium. Catalyst compositions found to be particularly suitable for catalysing the reaction of propylene, molecular oxygen and ammonia to produce acrylonitrile are those containing antimony, with additional metals chosen from tin, iron, copper, uranium, arsenic, vanadium and titanium.

When such additional metals are present the oxide composition may be regarded either as a mixture of the oxides of the various metals or as oxygen-containing compounds of such metals; under the reaction conditions either or both forms may be present and may be prepared by any known method such as by intimately mixing the oxides or compounds yielding the oxides on heating, or co-precipitation of the oxides, hydrated oxides or insoluble salts from an aqueous solution. The oxide composition is dried (if necessary), pelleted and heated in a molecular oxygen containing gas at a temperature between 700° and 900° C. The duration of the heat treatment may vary but is usually about 16 hours or more.

Thus, the complete composition may be prepared by precipitation of the oxides, hydroxides, etc. of all the components and heat treatment within the range 700° to 900° C. In this embodiment the molybdenum or tungsten components may be added to the remaining composition during the final washing stages of the latter in the form of solid compounds or aqueous solutions thereof. Alternatively, the constituents of the oxide composition excluding the Mo or W may first be prepared and heat-treated, then the heat-treated composition may be immersed in a solution of a heat-decomposable compound of Mo or W, e.g. ammonium molybdate or tungstate or molybdophosphoric acid or tungstophosphoric acid followed by drying. In a third method, the Mo or W additive may be introduced into the heat treated oxide composition by passing the vapour of a suitable compound of the additive over or through a bed of the oxide composition at an elevated temperature. Such a compound is, for example molybdic oxide.

The present invention is described in further detail with reference to the following example.

EXAMPLE

A basic catalyst was prepared by the following method to give the atomic proportions Sb/Sn/Cu/Fe/Ti = 3/1/0.25/0.25/0.25.

Antimony trioxide (438 parts by weight) was added to a heated (100° C) stirred mixture of water (1500 parts) and 70% nitric acid (531 parts), and this was followed by powdered tin (118.6 parts) added over 10 minutes. After cooling, the mixture was filtered and the cake was suspended in water (1300 parts). To the stirred mixture was added $Cu(NO_3)_2.3H_2O$ (60.6 parts) in water (200 parts), $Fe(NO_3)_3.9H_2O$ (101.4 parts) in water (200 parts), and n butyl titanate (83.8 parts) in dilute nitric acid (17% concentration, 240 parts), and the temperature was raised to 40° C. Aqueous ammonia was added until the pH was 6.3 and after stirring for 15 min. the mixture was cooled to room temperature and filtered. The cake was resuspended in water (2600 parts), filtered and dried. After pelleting to cylinders of 4 mm diameter and 4 mm length, the pellets were heat-treated in a furnace in which the temperature was raised at 22° C per hour and in which an air stream was injected at a rate of 50 liters/hour/Kg catalyst.

This basic composition and others prepared similarly (Nos. 6, 8, 10, 12, 14, 16, 18) were used to prepare catalysts according to the present invention as follows:

Catalysts Nos. 1 to 19

The basic composition in the form of heat treated pellets was soaked in an aqueous solution of ammonium molybdate for 16 hours, drained and dried. Catalysts containing uranium were prepared by incorporating during the preparation of the basic composition the appropriate quantity of uranly nitrate with the copper and iron nitrates prior to precipitation with ammonia. Catalysts containing vanadium were prepared by incorporating vanadium pentoxide in the wash stage of the basic composition preparation.

Catalysts Nos. 20 and 21

The molybdenum component was incorporated into the basic composition during preparation by addition of ammonium molybdate to the composition during the washing step.

Catalysts Nos. 22 and 23

The molybdenum component was incorporated into the basic composition as for catalysts Nos. 20 and 21 except that copper molybdate (catalyst No. 22) and molybdic oxide (catalyst No. 23) were used in place of ammonium molybdate.

Catalysts Nos. 24 and 25

The tungsten component was incorporated in the form of ammonium tungstate by soaking the heat treated pellets in an aqueous solution of ammonium tungstate for 16 hours, drained and drying.

Catalyst testing was carried out in a glass reactor with feed mixtures containing approximately 6% propylene, 6.5% ammonia, 68% air and 19.5% steam at a nominal contact time of 8 seconds, calculated from the total gas flow as N.T.P. and the volume of the empty reactor.

Product yields (molar) on propylene fed are shown in Tables I and II.

TABLE 1

| Catalyst No. | Sb | Sn | Catalyst Composition | | | | | Temperatures $-°C$ | | Yields (molar %) | | | | | | AN Efficiency % |
|---|---|---|---|---|---|---|---|---|---|---|---|---|---|---|---|---|
| | | | Cu | Fe | Ti | X | Mo | HT | Reaction | AN | AcO | HCN | $CO_2$ | CO | $C_3H_6$ | |
| Basic composition | 3 | 1 | 0.25 | 0.25 | 0.25 | — | — | 850 | 460 | 71.3 | 0.9 | 5.8 | 10.6 | 3.3 | 3.5 | 73.9 |
| 1 | 3 | 1 | 0.25 | 0.25 | 0.25 | — | 0.010 | 850 | 460 | 73.5 | 0.7 | 5.7 | 9.2 | 3.5 | 3.2 | 75.9 |
| 2 | 3 | 1 | 0.25 | 0.25 | 0.25 | — | 0.015 | 850 | 466 | 74.3 | 0.9 | 5.9 | 8.5 | 3.8 | 3.4 | 76.9 |
| 3 | 3 | 1 | 0.25 | 0.25 | 0.25 | — | 0.020 | 850 | 472 | 73.5 | 0.7 | 6.4 | 9.1 | 4.4 | 2.9 | 75.6 |
| 4 | 3 | 1 | 0.25 | 0.25 | 0.25 | — | 0.023 | 850 | 465 | 71.6 | 0.6 | 6.4 | 9.0 | 4.6 | 4.8 | 75.3 |
| 5 | 3 | 1 | 0.25 | 0.25 | 0.25 | — | 0.030 | 850 | 474 | 67.3 | 1.4 | 6.8 | 10.9 | 5.4 | 7.0 | 72.4 |
| 6 | 3 | 1 | 0.25 | 0.75 | 0.75 | — | — | 830 | 471 | 71.6 | 1.3 | 5.8 | 10.4 | 3.3 | 4.0 | 74.5 |
| 7 | 3 | 1 | 0.25 | 0.75 | 0.75 | — | 0.017 | 830 | 461 | 75.2 | 0.9 | 5.8 | 8.0 | 3.8 | 3.5 | 78.0 |
| 8 | 3 | 1 | 0.25 | 0.75 | 0.25 | — | — | 850 | 454 | 72.6 | 1.2 | 6.0 | 9.3 | 3.6 | 4.2 | 75.8 |
| 9 | 3 | 1 | 0.25 | 0.75 | 0.25 | — | 0.016 | 850 | 457 | 75.9 | 0.8 | 6.4 | 8.0 | 4.4 | 3.3 | 78.5 |
| 10 | 3 | 1 | 0.25 | — | 0.25 | — | — | 825 | 460 | 68.9 | 2.3 | 5.0 | 8.9 | 2.9 | 9.2 | 76.0 |
| 11 | 3 | 1 | 0.25 | — | 0.25 | — | 0.015 | 825 | 476 | 73.5 | 1.4 | 5.8 | 8.1 | 2.9 | 7.9 | 79.9 |
| 12 | 3 | 1 | 0.25 | 0.25 | 0.75 | 0.125V | — | 850 | 449 | 71.9 | 1.2 | 5.8 | 12.7 | 4.8 | 2.4 | 73.7 |
| 13 | 3 | 1 | 0.25 | 0.25 | 0.75 | 0.125V | 0.015 | 850 | 464 | 74.0 | 1.3 | 6.5 | 7.4 | 6.2 | 1.9 | 75.5 |
| 14 | 3 | 1 | 0.25 | 0.25 | 0.25 | 0.25U | — | 820 | 459 | 76.1 | 0.8 | 5.0 | 9.9 | 3.6 | 1.2 | 77.0 |
| 15 | 3 | 1 | 0.25 | 0.25 | 0.25 | 0.25U | 0.015 | 820 | 459 | 78.1 | 0.9 | 4.9 | 7.8 | 4.1 | 1.4 | 79.2 |
| 16 | 3 | — | 0.25 | — | 1 | 0.25U | — | 780 | 482 | 75.8 | 1.0 | 4.5 | 9.4 | 2.6 | 2.6 | 77.9 |
| 17 | 3 | — | 0.25 | — | 1 | 0.025U | 0.009 | 780 | 485 | 80.1 | 0.7 | 4.7 | 8.3 | 3.1 | 1.4 | 81.2 |
| 18 | 4 | 1 | — | 0.25 | — | — | — | 830 | 451 | 68.6 | 1.2 | 6.6 | 10.4 | 5.5 | 3.6 | 71.3 |
| 19 | 4 | 1 | — | 0.25 | — | — | 0.015 | 830 | 452 | 70.2 | 0.9 | 6.4 | 10.4 | 5.9 | 3.1 | 72.5 |
| 20 | 3 | 1 | 0.25 | 0.25 | 0.25 | — | 0.01 | 810 | 452 | 76.3 | 1.1 | 5.5 | 8.4 | 3.4 | 3.8 | 79.4 |
| 21 | 3 | 1 | 0.25 | 0.25 | 0.25 | 0.25U | 0.01 | 840 | 454 | 78.0 | 0.8 | 4.6 | 9.4 | 3.7 | 1.6 | 79.4 |
| 22 | 3 | 1 | 0.265 | 0.25 | 0.25 | | 0.015 | 810 | 459 | 74.6 | 1.0 | 5.1 | 9.1 | 4.0 | 4.0 | 77.7 |
| 23 | 3 | 1 | 0.25 | 0.25 | 0.25 | | 0.012 | 810 | 469 | 73.6 | 1.6 | 5.3 | 6.1 | 2.4 | 10.2 | 81.7 |

HT = Heat Treatment
AN = Acrylonitrile
AcO = Acrolein

TABLE II

| Catalyst No. | Sb | Sn | Cu | Fe | Ti | W | Temperatures °C | | Yields (molar %) | | | | | | AN Efficiency % |
|---|---|---|---|---|---|---|---|---|---|---|---|---|---|---|---|
| | | | | | | | HT | Reaction | AN | AcO | HCN | $CO_2$ | CO | $C_3H_6$ | |
| Basic composition | 3 | 1 | 0.25 | 0.25 | 0.25 | — | 850 | 460 | 71.3 | 0.9 | 5.8 | 10.6 | 3.3 | 3.5 | 73.9 |
| 24 | 3 | 1 | 0.25 | 0.25 | 0.25 | 0.010 | 850 | 468 | 73.9 | 1.0 | 6.0 | 9.1 | 4.4 | 1.8 | 75.2 |
| 25 | 3 | 1 | 0.25 | 0.25 | 0.25 | 0.015 | 850 | 472 | 73.5 | 0.8 | 6.1 | 9.3 | 4.8 | 1.2 | 74.5 |

We claim:
1. A catalyst oxide composition suitable for catalysing the reaction of organic compounds which consists essentially of oxygen and the elements antimony, tin, copper, iron, titanium and molybdenum or tungsten, and which has been heat treated at a temperature between about 700° and 900° C in a molecular oxygen-containing gas either before or after addition of the molybdenum or tungsten.

2. A catalyst as defined in claim 1 wherein said molybdenum or tungsten is present in the catalyst composition in an amount of from about 0.05 to 1.0 atom per cent.

3. A catalyst as defined in claim 1, which additionally contains uranium or vanadium.

4. A catalyst as defined in claim 2, which additionally contains uranium or vanadium.

5. A catalyst oxide composition suitable for catalysing the reaction of organic compounds which consists essentially of oxygen and the elements antimony, copper, titanium, molybdenum, and tin or uranium, and which has been heat treated at a temperature between about 700° and 900° C in a molecular oxygen-containing gas either before or after addition of the molybdenum.

6. A catalyst composition as defined in claim 5 wherein said molybdenum is present in the catalyst composition in a range of from about 0.05 to 1.0 atom percent.

* * * * *

UNITED STATES PATENT AND TRADEMARK OFFICE
CERTIFICATE OF CORRECTION

PATENT NO. : 3,990,999

DATED : November 9, 1976

INVENTOR(S) : EDWARD JAMES GASSON, THOMAS CHARLES KROSNAR and STANLEY FREDERIC MARRIAN It is certified that error appears in the above-identified patent and that said Letters Patent are hereby corrected as shown below:

Table 1, Catalyst No. "17", under the column "X", "0.025U" should read --0.25U--.

Signed and Sealed this

Third Day of January 1978

[SEAL]

Attest:

RUTH C. MASON
Attesting Officer

LUTRELLE F. PARKER
Acting Commissioner of Patents and Trademarks